United States Patent [19]

McRae

[11] Plant 4,175

[45] Jan. 3, 1978

[54] LILY PLANT: LILIUM 'FIRECRACKER'

[75] Inventor: Edward A. McRae, Boring, Oreg.

[73] Assignee: Melridge, Inc., Gresham, Oreg.

[21] Appl. No.: 761,225

[22] Filed: Jan. 21, 1977

[51] Int. Cl.[2] ..... A01H 5/00

[52] U.S. Cl. ..... Plt./68

[58] Field of Search ..... Plt./68

*Primary Examiner*—Robert E. Bagwill

*Attorney, Agent, or Firm*—Eugene D. Farley

[57] ABSTRACT

A new variety of Asiatic hybrid lily plant bearing large clusters of medium-sized flowers of excellent form, strong deep scarlet color, and long persistence, both on the plant and as a cut flower; the new plant particularly is characterized by its stately habit, relatively short foliage, its resistance to disease, tolerance of virus, and its vigor and multiplicative qualities. The plant has a very high bud count and superb bud color prior to the flowers opening. It is an excellent garden plant. The bulbs may be precooled and forced for cut flowers. The clone is very vigorous and is a good grower and propagator.

1 Drawing Figure

BACKGROUND OF THE INVENTION

My new variety of lily plant originated as a seedling selected from a group of seedlings at Gresham, Oreg. The seedlings resulted from a breeding program carried on by me since the year 1966. This program had as its objective the production of superior upright Asiatic lily clones for forcing for the cut flower trade. The characteristics sought were stately habit, relatively short foliage, high bud count, superior bud color prior to the flowers opening, and flowers of deep scarlet color.

I achieved the desired objective by using as the seed parent Lilium 'Harmony' (unpatented) and as the pollen parent Lilium 'Byam's Ruby' (unpatented).

My new lily plant is characterized by an erect and stately form, vigorous growth and excellent strength, with abundant, relatively short, lanceolate leaves of dark green color. It is a superior clone, both in physical appearance and in its uniform and rapid performance when forced out of season for the cut flower trade. The foliage is relatively short.

The plant possesses all of the desired characteristics of excellence of form, color and habit. It is highly resistant to disease and tolerant of virus. It produces a large number of buds having superior bud color prior to the flower opening. Numerous blooms of medium size are produced on a single stalk. The clone is vigorous and a good grower and propagator, as observed at Gresham, Oreg.

My new variety of lily plant has been asexually reproduced by me and under my direction at Gresham, Oreg. Successive generations produced by bulb scale propagation and natural propagation from bulblets and division have demonstrated that the novel and distinctive characteristics of my new variety are fixed and hold true with asexual propagation from generation to generation.

DESCRIPTION OF THE DRAWING

My new variety of lily plant is illustrated in the accompanying photographic drawing which shows the plant, the buds, and the open bloom in full color, thereby illustrating the flower form, the tepal arrangement, the connection of the flower to the stalk, the deep scarlet color of the flower, and the relatively short foliage.

DESCRIPTION OF THE NEW VARIETY

The following is a detailed description of my new variety of Asiatic hybrid lily, with nomenclature according to *The International Lily Register,* (Royal Horticultural Society, London, 2nd Edition, 1969), with color designations according to the Royal Horticultural Society Color Chart published by the R.H.S. in 1966.

THE PLANT

Origin: Seedling.

Parentage:

- *Seed parent.*—Lilium 'Harmony'.
- *Pollen parent.*—Lilium 'Byam's Ruby'.

Classification:

- *Botanic.*—Hybrid Lilium clone; Division I-A of Horticultural Classification of Lilies, R.H.S.
- *Commercial.*—Asiatic hybrid lily.

Form: Single stem, erect and stately.

Height: 28 to 35 inches when produced from bulbs 5 to 7 inches in circumference.

Growth: Very vigorous and upright.

Foliage:

- *Quantity.*—Abundant.
- *Size of leaf.*—2 to 4 inches long.
- *Shape of leaf.*—Lanceolate.
- *Texture.*—Leathery and glossy.
- *Color.*—Dark green on both upper side and under side.

Bulbs:

- *Size.*—Any size, ranging up to 10 inches in circumference.
- *Color.*—White.

THE BUD

Form: Obtuse, urn-shaped and long.

Size: 2 to 2½ inches long, and 1½ inches in circumference at maturity.

Opening: Bud opens slowly.

Color: Deepest scarlet when tepals first divide and also when tepals begin to unfurl.

Tepals: Curl back; deepest scarlet both inside and outside.

Peduncle: 1 to 2 inches long; erect; dark green with reddish tinge in color.

THE FLOWER

Blooming habit: Recurrent; blooms annually in mid-season; blooms once and profusely.

Size: Medium; about 5 inches in diameter.

Borne: In clusters, from 10 to 35 blooms on a single stem, approximately 14 produced by 5 to 6 inch bulbs or 8 from a 4 to 5 inch bulb.

Shape: Flat, without substantial change in shape during the blooming period.

Tepalage:

*Number of tepals.*—6.

*Arrangement.*—Imbricated.

*Color.*—Deepest scarlet at outer tepal and base; deepest scarlet with a few small spots at the inside of the tepal; and deepest scarlet on the reverse side. The deep scarlet tone is characterized by values of R.H.S. C.C.34A at the centers of the tepals diffusing to R.H.S. C.C.33B at the margins, with hairline margins of R.H.S. C.C.25A, under normal full daylight lighting conditions. Nectary furrow margins are covered with white pubescence.

*Tepal longevity.*—Tepals stay on stem about 3 weeks.

Pedicel:

*Length.*—1 to 3 inches, secondary pedicals 1 to 1½ inch.

*Color.*—A deepest green with reddish tinge.

*Form.*—Pedicel is sturdy and upright.

Color permanence: Color intensifies with age.

Appearance: The flower is shiny.

Disease resistance: The flower and plant are resistant to disease; in particular, they are resistant to Fusarium and Botrytis.

Fragrance: The flower is not fragrant.

Lasting quality: The flower is long lasting both on the plant and as a cut flower.

THE REPRODUCTIVE ORGANS

Stamens, anthers:

*Arrangement.*—Typical of Liliaceae.

*Length.*—2 inches.

*Number.*—6.

*Filaments.*—Length, 2 inches; color, soft cream.

Pollen: Chocolate brown in color.

Pistils: One in number with a length of about 2 inches.

Stigma: Soft cream in color.

Characteristics of ovaries: Typical of genus Lilium.

FRUIT

Fertility: The fruit is fertile.

Shape: The fruit is ovoid in shape.

Color at maturity: The fruit is soft brown.

My new variety of lily most closely resembles Lilium 'Cinnabar', but is distinguished therefrom in its shorter foliage, greater number of flowers, deeper bud color and superior forcing characteristics.

I claim:

1. A new and distinctive variety of Asiatic hybrid lily plant substantially as herein shown and described, characterized by its stately habit, relatively short foliage, high bud count, deep bud color, its great resistance to disease; its high tolerance of viral infection; the vigorous growth and propagative characteristics of its clone; its rapid growth and suitability for forcing; its excellent bud color prior to the flowers opening; and the deep scarlet color of its flowers.

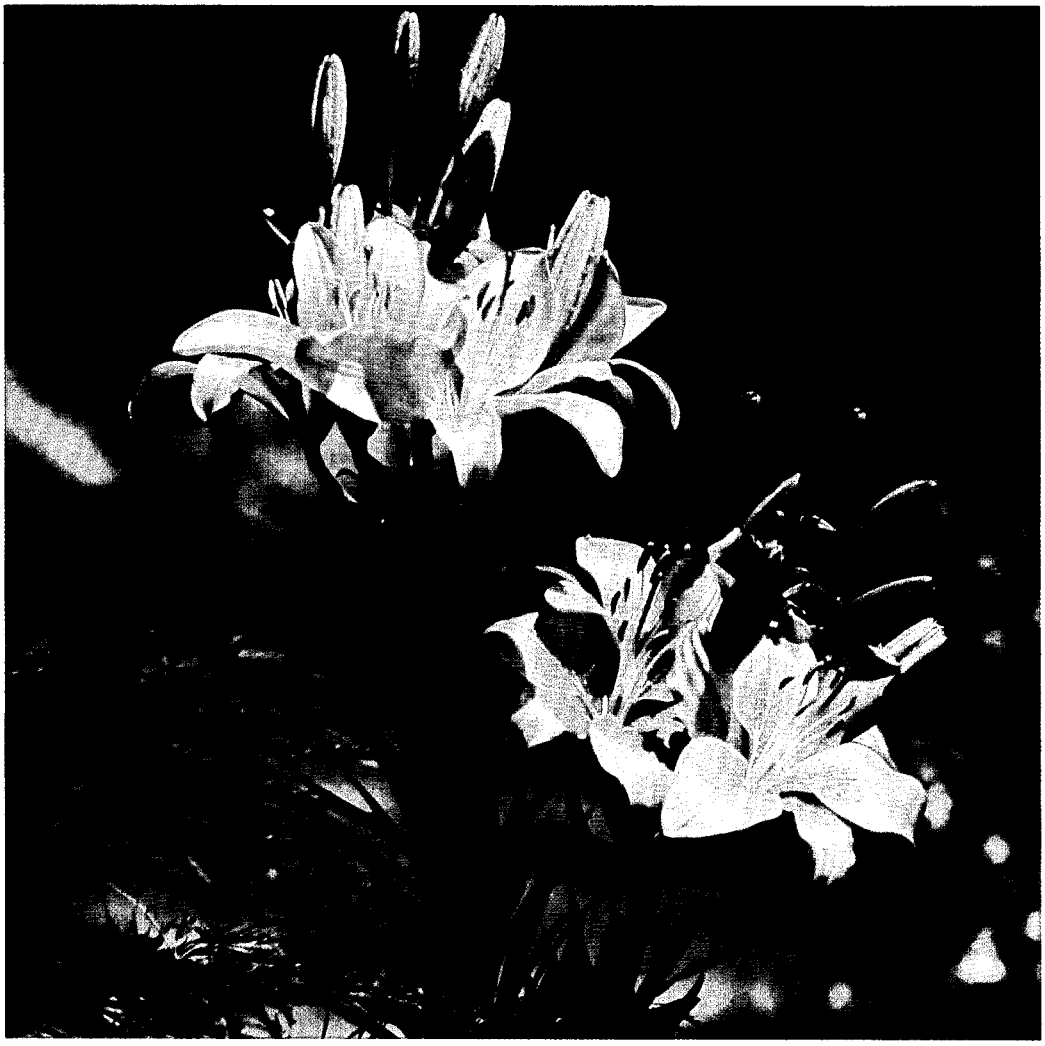

* * * * *